US009561578B2

(12) United States Patent
Geyer et al.

(10) Patent No.: US 9,561,578 B2
(45) Date of Patent: Feb. 7, 2017

(54) METHOD OF ORTHOPAEDIC IMPLANT FINISHING

(71) Applicant: Smith & Nephew, Inc., Memphis, TN (US)

(72) Inventors: Christopher D Geyer, Memphis, TN (US); Terry N Babb, Olive Branch, MS (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/404,756

(22) PCT Filed: May 31, 2013

(86) PCT No.: PCT/US2013/043559
§ 371 (c)(1),
(2) Date: Dec. 1, 2014

(87) PCT Pub. No.: WO2013/181504
PCT Pub. Date: Dec. 5, 2013

(65) Prior Publication Data
US 2015/0111473 A1  Apr. 23, 2015

Related U.S. Application Data

(60) Provisional application No. 61/654,176, filed on Jun. 1, 2012, provisional application No. 61/705,315, filed on Sep. 25, 2012.

(51) Int. Cl.
*B24C 1/00* (2006.01)
*B24C 1/08* (2006.01)
*B24C 1/10* (2006.01)
*A61F 2/30* (2006.01)
*B24C 3/22* (2006.01)
*B24C 7/00* (2006.01)

(52) U.S. Cl.
CPC ............. *B24C 1/08* (2013.01); *A61F 2/30767* (2013.01); *B24C 1/10* (2013.01); *B24C 3/22* (2013.01); *B24C 7/0023* (2013.01); *A61F 2002/30906* (2013.01)

(58) Field of Classification Search
CPC .......... B24C 1/10; B24C 3/22; B24C 27/0023; B24C 1/08; A61F 2/30767
USPC ...................................... 451/36–40
See application file for complete search history.

(56) References Cited

U.S. PATENT DOCUMENTS 3,416,934 A * 12/1968 McNair .................... B24C 1/00
106/266
4,644,942 A * 2/1987 Sump .................. A61F 2/30767
29/423

(Continued)

OTHER PUBLICATIONS

Tool and Manufacturing Engineers Handbook, Desk Edition, 1989, pp. 45-24: 45-25.

*Primary Examiner* — George Nguyen
(74) *Attorney, Agent, or Firm* — Taft Stettinius & Hollister LLP

(57) ABSTRACT

A process to effectively remove machine lines blending the surface to a high luster uniform visual standard while reducing the surface roughness to below 8 Micro inches. The process does not remove or move the affected material greater than 0.02 mm, and the process is designed to produce a visually acceptable part that reduces surface roughness below 8 micro inches and holds tightly toleranced complex geometries.

22 Claims, 3 Drawing Sheets

(56) References Cited

U.S. PATENT DOCUMENTS

| | | | | |
|---|---|---|---|---|
| 4,669,230 | A * | 6/1987 | Suzuki | B24C 7/0015 |
| | | | | 451/100 |
| 5,018,320 | A * | 5/1991 | Anguelo | B24C 3/325 |
| | | | | 451/82 |
| 5,251,468 | A * | 10/1993 | Lin | A61F 2/30767 |
| | | | | 29/90.7 |
| 5,573,445 | A * | 11/1996 | Rasmussen | B08B 3/12 |
| | | | | 430/127 |
| 5,709,587 | A * | 1/1998 | Shaffer | B24B 1/00 |
| | | | | 451/38 |
| 6,422,920 | B1 * | 7/2002 | Bouten | B24C 1/04 |
| | | | | 451/29 |
| 6,634,928 | B2 * | 10/2003 | Erickson | B24C 1/045 |
| | | | | 451/38 |
| 8,926,399 | B2 * | 1/2015 | Asai | B24C 1/00 |
| | | | | 451/102 |
| 2003/0124955 | A1 * | 7/2003 | Hanson | B24C 3/04 |
| | | | | 451/2 |
| 2005/0121417 | A1 * | 6/2005 | Dixon | A61F 2/30767 |
| | | | | 216/88 |
| 2007/0107182 | A1 * | 5/2007 | Sutton | A61F 2/30767 |
| | | | | 29/407.05 |
| 2008/0142050 | A1 * | 6/2008 | Hashish | B24C 3/325 |
| | | | | 134/22.12 |
| 2009/0088858 | A1 * | 4/2009 | Zinger | A61F 2/30767 |
| | | | | 623/18.11 |
| 2009/0189312 | A1 * | 7/2009 | Hall | A61C 3/025 |
| | | | | 264/313 |
| 2012/0021675 | A1 * | 1/2012 | Matsui | B24B 37/044 |
| | | | | 451/36 |
| 2013/0174607 | A1 * | 7/2013 | Wootton | B23K 26/0042 |
| | | | | 65/29.18 |

\* cited by examiner

METHOD OF ORTHOPAEDIC IMPLANT FINISHING

CROSS-REFERENCE TO RELATED APPLICATIONS

This application is a United States National Phase filing of International Application No. PCT/US2013/043559, which claims the benefit of U.S. Provisional Application No. 61/654,176, filed on Jun. 1, 2012, and U.S. Provisional Application No. 61/705,315 filed on Sep. 25, 2012. The disclosure of each application is incorporated by reference in its entirety.

BACKGROUND OF THE INVENTION

Field of the Invention

Embodiments of the present invention generally relate to orthopaedic implants, and particularly to methods of surface finishing an orthopaedic implant.

The present invention relates generally to To maximize the life of a prosthesis, the accuracy of the dimensional characteristics of the components of the prosthesis as well as the surface condition, for example the surface finish, is extremely critical in the life of the prosthesis. Dimensional errors and surface finish imperfections may cause the prosthesis to prematurely wear. The components that wear on the prosthesis, particularly those that wear rapidly, may lead to reactions with the tissues of the body. Such reaction to foreign objects is called osteolysis. Osteolysis can damage soft tissue and further complicate the replacement of the prosthesis.

Attempts have been made to provide for improved finishes and geometries of the articulating surface of a prosthesis. For example, the surfaces may be polished by hand by, for example, a rubbing compound or by a metal or cloth buffing wheel. Alternatively, the surfaces may be smoothed by robotic manipulators using similar tools as are used by hand. Alternatively, the components have the articulating surface of the prosthesis may be polished by a finishing orthopaedic implant, for example a tumbling machine. These prior art attempts at providing improved geometry and finish to the articulating surface of a prosthetic component are slow and inaccurate. Further, attempts to improve the finish on the part may affect its geometry or shape Imperfections in shape and or finish may greatly reduce the operating life of the prosthesis and may lead to osteolysis.

Previously, surface finishing implemented to produce low Ra values and uniform finish was performed through a manual process with grinding tools and polishing compound to remove belt lines and smooth out the surface. Variations produced by the prior art process had many contributing factors causing variation throughout the orthopaedic implant and also between batches. As examples, these variations were caused by operator skill, applied pressure, condition of grinding tools, amount of compound, and total process time. Those variables caused orthopaedic implants to be inconsistent, and the surface finish was left exposed to many possible failure modes (scratches, nicks, and waviness).

There remains a need in the art for orthopaedic implants that maintain dimensional integrity throughout complex geometries under 0.02 mm through a finishing process that effectively removes machine lines, has a uniform luster appearance, and yields a surface roughness Ra less than 8 micro inches.

SUMMARY OF THE INVENTION

It is in view of the above problems that the present invention was developed. The invention is a process to effectively remove machine lines blending the surface to a high luster uniform visual standard while reducing the surface roughness to below 8 Micro inches. The process does not remove or move the affected material greater than 0.02 mm, and the process is designed to produce a visually acceptable part that reduces surface roughness below 8 micro inches and holds tightly toleranced complex geometries.

In one aspect of the invention, to orthopaedic surgeons, the process provides an implant with improved function through a tighter fit. The tighter fit reduces the chance of disassociation and reduces the chance of micro motion. The tighter fit is obtained by removing less material in comparison to hand finishing, thus resulting in a component that is closer to nominal dimensions. Further, the process provides a more consistent visual appearance and more consistent locking geometry. The disclosed process reduces visual aesthetic rejection, thereby saving manufacturing costs. Finally, it is believed the disclosed process provides an increased strength of the component through a peening effect on the surface.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings.

DETAILED DESCRIPTION OF THE EMBODIMENTS

Figure 1:
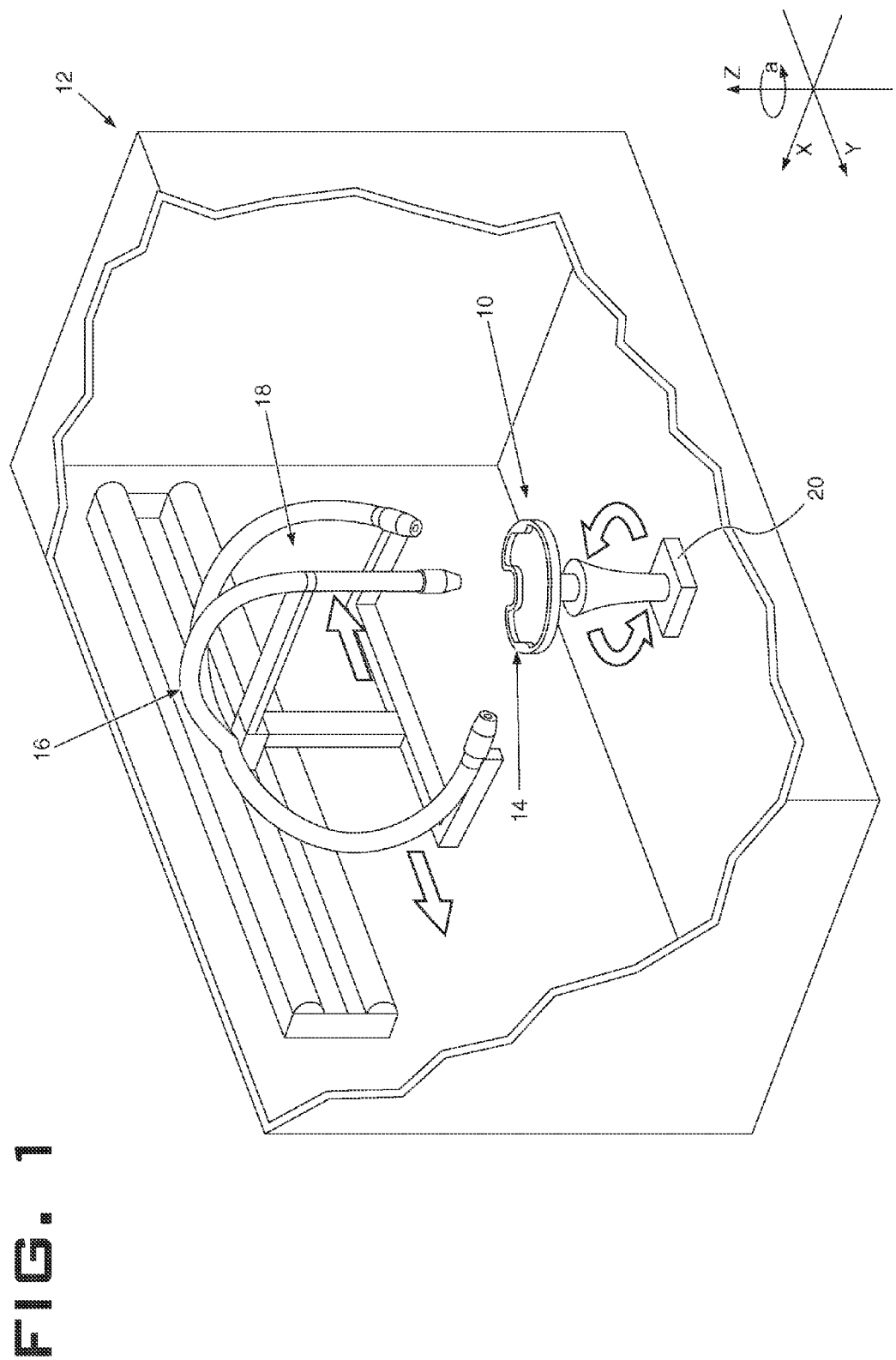
FIG. 1 is a perspective view of an orthopaedic implant fixtured in a wet blasting cabinet.

Referring to the accompanying drawings in which like reference numbers indicate like elements, FIG. 1 illustrates embodiments of the present invention and provide a process to effectively remove machine lines blending the surface to a high luster uniform visual standard while reducing the surface roughness to below 8 micro inches. FIG. 1 shows a perspective view of an orthopaedic implant 10 fixtured in a wet blasting cabinet 12. As examples, the orthopaedic implant 10 may be a knee prosthesis, a hip prosthesis, a shoulder prosthesis, or a spine prosthesis. The disclosed process is specific to wet blasting. The orthopaedic implant 10 is inserted into the wet blast cabinet 12 and a slurry mixture is applied to a targeted surface 14 of the orthopaedic implant 10 at a specified pressure. In some embodiments, the pressure ranges from about 15 to about 60 pounds per square inch (psi) and more narrowly from about 35 to about 50. In the depicted embodiment, the specified pressure is about 50 psi. In some embodiments, the slurry mixture is heated from about 40 to about 100 degrees Fahrenheit, and more narrowly from about 70 to about 80 degrees Fahrenheit.

The overall force of the wetblast is a combination of both the air pressure (controlled by an air regulator) and slurry pressure. The slurry pressure is created by a motor driven impeller that does not have active control for revolutions per minute. Fluctuations in impeller speed directly affect variation in the slurry pressure. The default slurry pressure created by the impeller is approximately 30 psi. With the variation caused by the motor the slurry pressure can gain or drop directly affecting the overall blasting force. At higher pressure ranges (e.g., 50 psi) the process is significantly more stable. The increased air pressure has a greater influence over the combined blast force resulting in a more stable process. The effect of the motor variation is overcome by additional air pressure and distance to the part.

Figure 3:
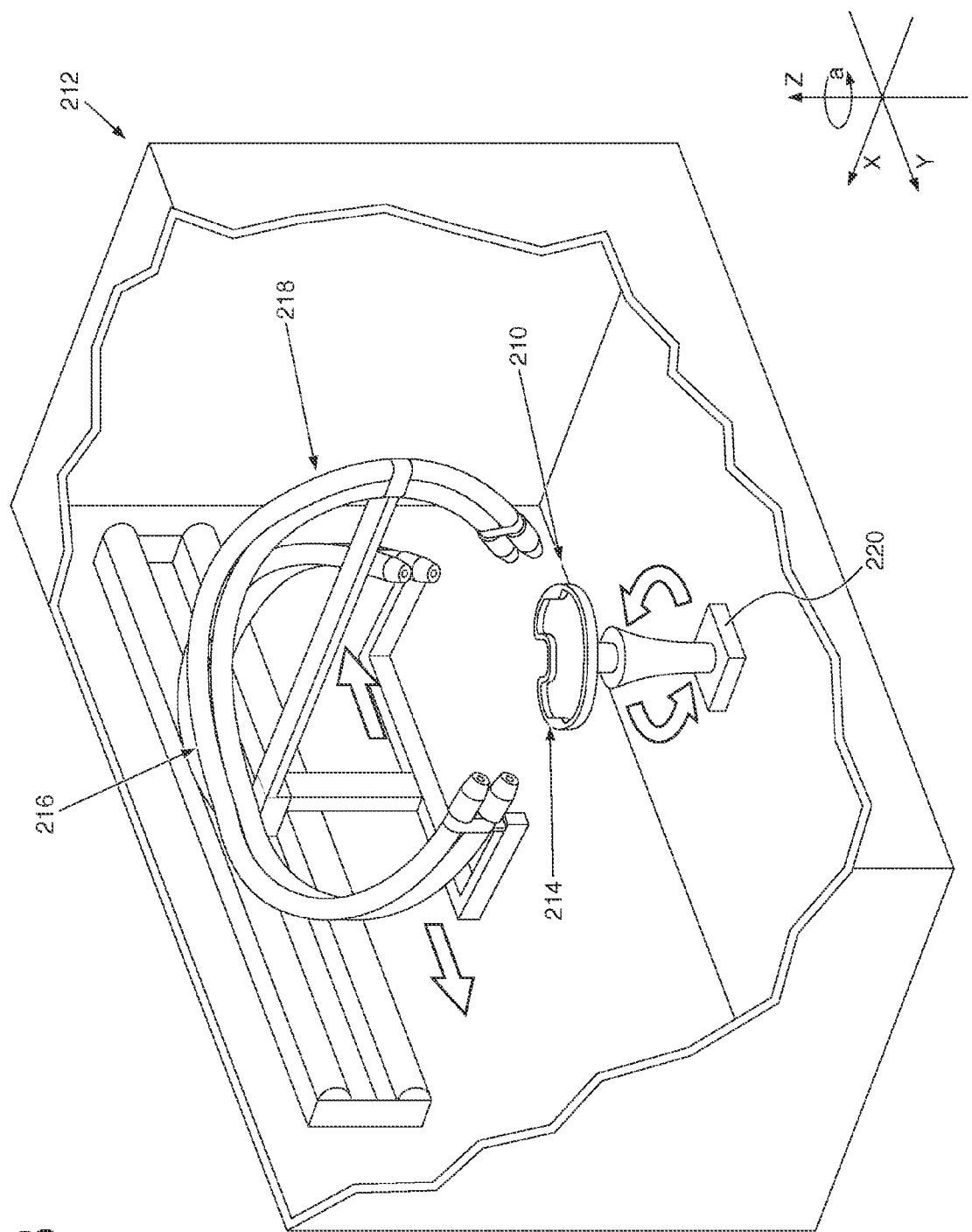
FIG. 3 is a perspective view of an orthopaedic implant fixtured in a wet blasting cabinet in a second alternative arrangement.

The wet blasting cabinet 12 includes an arm 16 with at least one blast nozzle 18. In the depicted embodiment, there are three blast nozzles 18, but any number of blast nozzles may be used. For example, there may be from one to six blast nozzles depending upon the size and/or shape of the implant. As best seen in FIG. 3, some blast nozzles may be provided in pairs in some embodiments. The blast nozzles 18 are generally located a distance from about 0.25 inches to about 18 inches away from the orthopaedic implant 10 and more narrowly from about three inches to about twelve inches. In the depicted embodiment, the distance from the nozzles 18 to the targeted surface 14 is about 11.25 inches. The nozzle 18 may provide a solid stream spray or a full cone, but other spray patterns may equally be applicable. In the depicted embodiment, each nozzle 18 has a bore of about 0.5 inches in diameter, but bores from about 0.25 inches to about 1 inch in diameter may be used. In an alternative embodiment the nozzle 18 has a bore of about 0.375 inches. In the depicted embodiment, each nozzle 18 has a length of about 1.5 inches, but lengths from about 0.5 inches to about 3 inches may be used.

Figure 2:
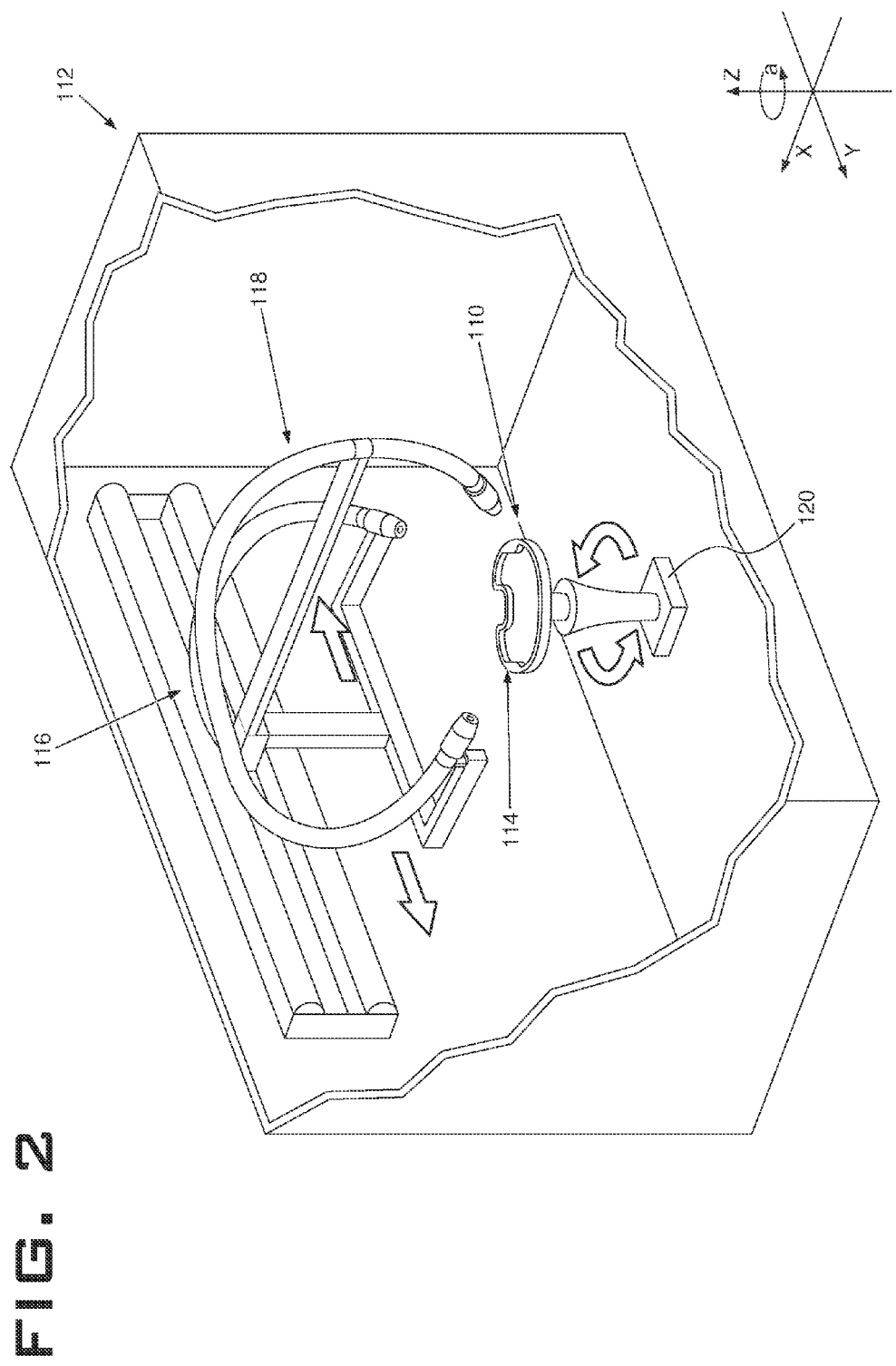
FIG. 2 is a perspective view of an orthopaedic implant fixtured in a wet blasting cabinet in a first alternative arrangement.

FIGS. 1-3 illustrate various blast nozzle configurations. In some embodiments, multiple blast nozzles directed at the part may interfere with one another, thereby losing blast effectiveness and causing prolonged cycle time or insufficient final part appearance. In some embodiments, the blast pattern for each individual nozzle may be targeted such that it does not interfere with a blast pattern of another nozzle. If the nozzle blast patterns directly interfere with one another or reflect off the target area into another blast pattern the effectiveness of the blast force may be compromised. The nozzles may be fixtured parallel to one another to effectively grow the target area on the part while also limiting the nozzle blast pattern interference.

The orthopaedic implant 10 is wet blasted through a series of movements to effectively remove machine lines and blend the surface to an aesthetic uniform finish. The process includes the steps of fixturing the orthopaedic implant 10 to a platform 20 that rotates in one degree of freedom "a," and the work being done to the orthopaedic implant 10 is applied in a parallel plane traversing across "x" "y" and/or "z" axis. The blast nozzles 18 move back and forth while the orthopaedic implant 10 rotates to ensure coverage of the entire surface. In some embodiments, the arm 16 moves in a linear direction at a speed of from about 10 inches to about 60 inches per minute. In some embodiments, the platform 20 rotates at about 5 to about 360 revolutions per minute (RPMs) and more narrowly from about 5 to about 20 RPMs. In some embodiments, the blast nozzles 18 are stationary and only the platform 20 rotates. Alternatively, the platform 20 is stationary and the blast nozzles 18 move. In yet another embodiment, the blast nozzles 18 and/or the platform 20 move at predetermined intervals. The angle of impaction of the slurry mixture onto the targeted surface 14 is significant. An angle of about ninety degrees is used to smooth machine lines and an angle of about forty-five degrees is used to blend the entire surface. In one embodiment, the angle of impaction is maintained at sixty degrees throughout the cycle. The entire cycle time is less than five minutes in some embodiments.

The slurry mixture is generally made from water and media. The slurry mixture has a media concentration of about 5 percent to about 35 percent. In the depicted embodiment, the slurry mixture has about 23 percent media concentration. The media is between about 0.001 mm and about 0.125 mm in size. In some embodiments, the media is generally about eighty-five percent spherical. In some embodiments, the media is made from ceramic beads. As an example, media such as Microblast B125 or B205 may be used. Microblast is a registered trademark of Saint-Gobain Zirpro, which is a division of the Saint-Gobain Ceramic Materials Division. Without being tied to any specific theory, it is believed the process is successful because the media is transferred in water which cushions the blast, thereby reducing the amount of material movement. The process has been developed to work on titanium alloys, and more specifically to Ti-6Al-4V, but may be applicable to other materials. The process could be applied to any size, shape, or complex geometry orthopaedic implant that needs to maintain dimensional integrity within about 0.02 mm (or 0.00075 inches). The process is valuable to orthopaedic implants requiring a uniform luster appearance with low surface roughness with tightly toleranced complex geometries.

The term "about" as used herein may be applied to modify any quantitative representation which could permissibly vary without resulting in a change in the basic function to which it is related. For example, the slurry mixture pressure as disclosed herein as being applied from about 35 to about 50 psi may permissibly vary 0-4 psi within the scope of the invention if the function of providing a uniform luster appearance with low surface roughness is not materially altered.

In view of the foregoing, it will be seen that the several advantages of the invention are achieved and attained. The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, while the figures illustrate a knee prosthesis, the invention may apply to any type of medical device. Thus, the breadth and scope of the present invention should not be limited by any of the above-described exemplary embodiments, but should be defined only in accordance with the following claims appended hereto and their equivalents.

What is claimed is:

1. A method of surface finishing an orthopaedic implant comprising:
    a. fixturing a machined orthopaedic implant having a targeted surface with machine lines on a platform in a wet blasting cabinet, the wet blasting cabinet having at least one nozzle;
    b. rotating the platform at a speed of about 5 to about 360 revolutions per minute;
    c. moving the at least one nozzle and the platform relative to one another in a linear motion at a speed of 10 to 60 inches per minute; and
    d. applying a slurry mixture at an impaction angle to the targeted surface through the at least one nozzle at pressure of 15 to 60 pounds per square inch to effectively remove the machine lines blending the targeted surface, wherein the pressure is a combination pressure of both air pressure and slurry pressure, and wherein the at least one nozzle is located from about 0.25 inches to about 18 inches away from the targeted surface, and the at least one nozzle has a bore from about 0.25 inches to about 0.50 inches in diameter.

2. The method of claim 1 wherein the pressure is about 35 to about 50 pounds per square inch.

3. The method of claim 1 wherein the pressure is 50 pounds per square inch.

4. The method of claim 1 wherein the slurry pressure is created by a motor driven impeller.

5. The method of claim 1 wherein the slurry pressure is 30 psi.

6. The method of claim 1 wherein the at least one nozzle is located at 11.25 inches from the targeted surface.

7. The method of claim 1 wherein the at least one nozzle provides a solid stream or full cone spray pattern.

8. The method of claim 1 wherein the at least one nozzle has a bore of about 0.375 inches.

9. The method of claim 1 wherein the at least one nozzle has a length from about 0.5 inches to about 3 inches.

10. The method of claim 1 wherein the at least one nozzle has a length of about 1.5 inches.

11. The method of claim 1 wherein the platform rotates at about 5 to about 20 revolutions per minute.

12. The method of claim 1 wherein the impaction angle is selected from the group consisting 45, 60, and 90 degrees.

13. The method of claim 1 wherein the media is between about 0.001 and about 0.125 mm in size.

14. The method of claim 1 wherein the media is about 85 percent spherical.

15. The method of claim 1 wherein the slurry mixture is heated from about 40 to about 100 degrees Fahrenheit.

16. The method of claim 1 wherein the slurry mixture is heated from about 70 to about 80 degrees Fahrenheit.

17. The method of claim 1 wherein there are three nozzles.

18. The method of claim 17 wherein the three nozzle do not interfere with one another.

19. The method of claim 1 wherein the slurry mixture is made from water and media and has a media concentration of about 5 to about 35 percent.

20. The method of claim 19 wherein the slurry mixture has a media concentration of 23 percent.

21. A method of surface finishing an orthopaedic implant comprising:
    a. fixturing a machined orthopaedic implant having a targeted surface with machine lines on a platform in a wet blasting cabinet, the wet blasting cabinet having at least one nozzle, the at least one nozzle has a bore from about 0.25 inches to about 0.50 inches in diameter, and the at least one nozzle has a length from about 0.5 inches to about 3 inches;
    b. rotating the platform at a speed of about 5 to about 20 revolutions per minute;
    c. moving the at least one nozzle and the platform relative to one another in a linear motion at a speed of 10 to 60 inches per minute;
    d. heating a slurry mixture in a range from about 70 to about 80 degrees Fahrenheit, the slurry mixture is made from water and media, the media has a media concentration of about 5 to about 35 percent, and the media is between about 0.001 and about 0.125 mm in size; and
    e. applying the slurry mixture at an impaction angle to the targeted surface through the at least one nozzle at pressure of 30 to 50 pounds per square inch to effectively remove the machine lines blending the targeted surface, wherein the pressure is a combination pressure of both air pressure and slurry pressure, and the impaction angle is selected from the group consisting 45, 60, and 90 degrees.

22. A method of surface finishing an orthopaedic implant comprising:
    a. fixturing a machined orthopaedic implant having a targeted surface with machine lines on a platform in a wet blasting cabinet, the wet blasting cabinet having at least three nozzles, the at least three nozzles are each located from about 0.25 inches to about 18 inches away from the targeted surface, and the at least three nozzles each has a bore from about 0.25 inches to about 0.50 inches in diameter, and the at least three nozzles each has a length from about 0.5 inches to about 3 inches;
    b. rotating the platform at a speed of about 5 to about 20 revolutions per minute;
    c. moving the at least three nozzles and the platform relative to one another in a linear motion at a speed of 10 to 60 inches per minute;
    d. heating a slurry mixture in a range from about 70 to about 80 degrees Fahrenheit, the slurry mixture is made from water and media, the media has a media concentration of about 5 to about 35 percent, and the media is between about 0.001 and about 0.125 mm in size; and
    e. applying the slurry mixture at an impaction angle to the targeted surface through the at least three nozzles at pressure of 30 to 50 pounds per square inch to effectively remove the machine lines blending the targeted surface, wherein the pressure is a combination pressure of both air pressure and slurry pressure, and the impaction angle is selected from the group consisting 45, 60, and 90 degrees.

* * * * *